United States Patent [19]

Gray

[11] Patent Number: 4,828,491
[45] Date of Patent: May 9, 1989

[54] UNITARY PREASSEMBLED DISPOSABLE INTRA-ORAL RUBBER DAM DEVICE

[75] Inventor: Norman Gray, Cary, N.C.
[73] Assignee: Aukland Group, Inc., Cary, N.C.
[21] Appl. No.: 172,521
[22] Filed: Mar. 24, 1988
[51] Int. Cl.⁴ ............................................. A61C 5/14
[52] U.S. Cl. ......................................................... 433/136
[58] Field of Search ................................. 433/136, 127

[56] References Cited

U.S. PATENT DOCUMENTS 3,781,994  1/1974  Hesselgren ..................... 433/137
4,600,387  7/1986  Ross ................................ 433/136

*Primary Examiner*—Robert Peshock
*Attorney, Agent, or Firm*—John C. Smith, Jr.

[57] ABSTRACT

A unitary preassembled disposable intra-oral rubber dam device comprises an annular resilient frame member such as a resilient plastic cord frame, and an elastic latex membrane, the perimeter of the membrane being secured to the frame member such that the membrane is maintained in substantially the same plane as the frame member. The annular frame member, having a predetermined configuration, has a memory characteristic such that when pressure applied to distort the frame member is relaxed the frame member returns to substantially its predetermined configuration.

12 Claims, 2 Drawing Sheets

U.S. Patent   May 9, 1989   Sheet 1 of 2   4,828,491
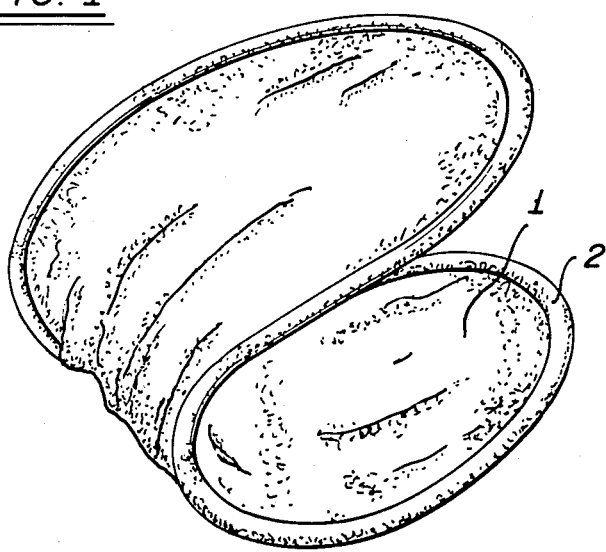
FIG. 1
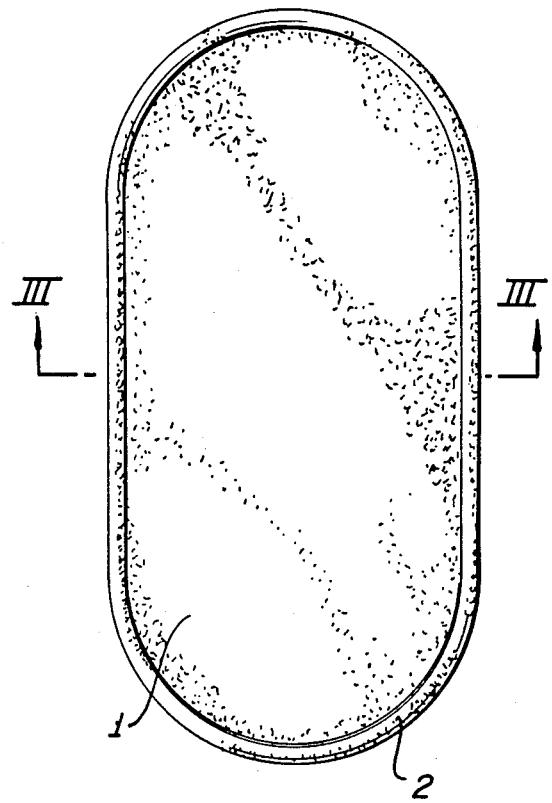
FIG. 2
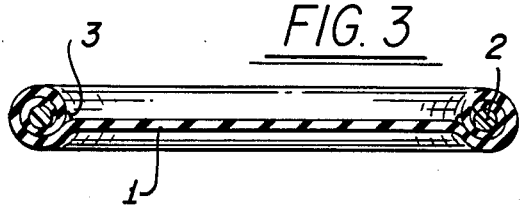
FIG. 3
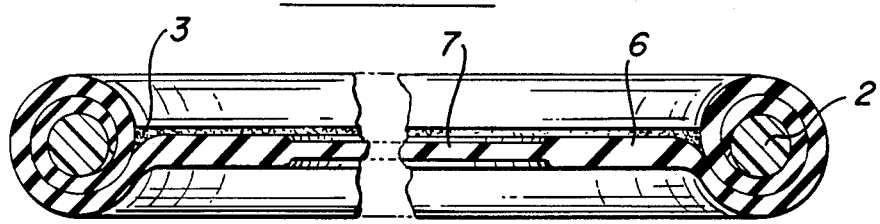
FIG. 4
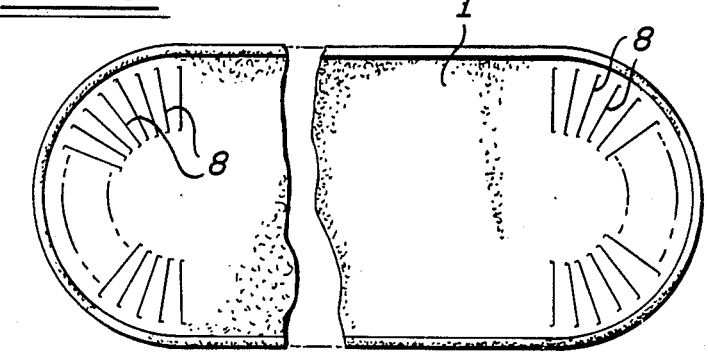
FIG. 5
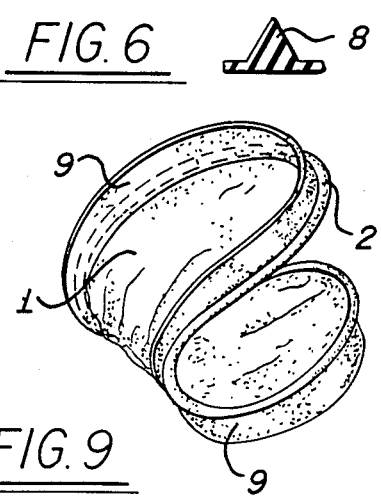
FIG. 6
FIG. 9

UNITARY PREASSEMBLED DISPOSABLE INTRA-ORAL RUBBER DAM DEVICE

BACKGROUND OF THE INVENTION

The present invention relates to a preassembled intra-oral disposable rubber dam device for use during dental procedures.

Rubber dams for use during various dental procedures are well known. The dams comprise a thin rubber sheet material which is stretched over a frame and anchored with one or more clamps. The dentist or dental technician cuts one or more small apertures in the dam corresponding to the location of one or more teeth on which a dental procedure is to be carried out. The perforated dam is then inserted in the patient's oral cavity and stretched over said one or more teeth causing said teeth to project through the perforations. The dam permits a dental procedure to be carried out on the one or more projecting teeth while at the same time preventing foreign objects from being deposited in other portions of the patient's oral cavity and passing down the patient's throat. Also, the dam serves to keep the isolated one or more teeth and surrounding area aseptic.

Prior art rubber dams are illustrated and described, for example, in the following U.S. patents:

629,324—Allen
663,507—Meguiar
802,711—Schrader
1,579,608—Haudenshield
1,604,136—Stoloff
1,292,133—Stoughton
3,781,994—Hessengren
4,544,357—Williams
4,600,387—Ross Prior art rubber dams have a number of disadvantages. They are awkward to use and are uncomfortable for the patient. The rubber dams have required the utilization of demountable frames and clamps which are difficult and time-consuming to use and add to patient discomfort. The frames have protrusions which occasionally project into the patient's nostrils or cheeks. The clamps are spring devices which, when installed on teeth, squeeze the delicate gum tissue around the tooth, requiring local anesthesia to suppress the pain. Furthermore, many prior art rubber dams must be removed before X-rays can be taken and then reinstalled, necessitating removal and reinstallation of the clamps which bite into gum tissue. The clamps are required to retain the rubber dam in place. The frames of prior art rubber dams maintain the rubber dams under tension, tending to draw the rubber dam off the projecting teeth and out of the oral cavity. The clamps, secured in place on usually several teeth, assure that the rubber dam will stay in place in the oral cavity with the teeth projecting through the perforations in the dam. The present invention avoids these and other disadvantages of prior art rubber dams.

It is a principal object of the invention to provide an effective, preassembled rubber dam device for use in any and all dental procedures.

Another object of the invention is to provide a preassembled rubber dam device at sufficiently low cost that it is disposable.

Another object of the invention is to provide a convenient rubber dam device that needs no separate external or internal frames and no clamps for the isolation of a tooth or series of teeth.

Another object of the invention is to provide a rubber dam device which, when positioned in the oral cavity with one or more teeth projecting through perforations therein, will remain in place without the need for clamps or other devices.

A still further object of the invention is to provide a comfortable rubber dam device for the patient which will allow the patient to swallow during the dental operative procedure but prevent the patient from swallowing or aspirating foreign objects.

A still further object of the invention is to provide a rubber dam device that allows the dentist or dental technician to take X-rays of the oral cavity and/or its contents without first removing the device.

A still further object of the invention is to give the dentist or dental technician a rubber dam device which gives him/her the choice of protecting and retracting the patient's lips or to having the device installed in an intra-oral fashion.

Another object of the invention is to provide the dentist or dental technician with a rubber dam device that assures a constant open oral cavity such that the dentist or dental technician does not need to continually ask or remind the patient to open his/her mouth.

A still further object of the invention is to provide a dentist or dental technician with a rubber dam device which will allow the dentist or dental technician to work simultaneously in more than one quadrant of the operative field.

Another object of the invention is to provide a dentist or dental technician with a rubber dam device which will assist the dentist or dental technician with management of difficult and/or pediatric patients without loss of comfort for the patient.

These and other objects and advantages of the present invention will become apparent from the following detailed description when read in conjunction with the drawings.

SUMMARY OF THE INVENTION

The present invention is a unitary preassembled disposable intra-oral rubber dam device basically comprising an elastic membrane held taut about its periphery by a complementary annular spring-like frame member. The frame member has the necessary resilience such that when the rubber dam device is folded the spring-like frame member will bias the rubber dam device towards a substantially flat configuration. The spring-like frame member, due to its resilient nature, assures that the elastic membrane will be retained in position in the oral cavity of the patient with one or more teeth projecting through apertures therein without the need for clamps and external frame members. Furthermore, the spring-like frame member serves to press against the internal surfaces of the patient's cheeks to assure that foreign objects and fluids do not bypass the rubber dam and enter other portions of the oral cavity.

BRIEF DESCRIPTION OF THE DRAWINGS

FIG. 1 is a perspective view of an embodiment of the preassembled intra-oral disposable rubber dam device of the present invention;

FIG. 2 is a plan view of the rubber dam device shown in FIG. 1;

FIG. 3 is a cross-sectional view of the rubber dam device taken along the line III—III of FIG. 2;

FIG. 4 is a cross-sectional view of another embodiment of the preassembled intra-oral disposable rubber dam device of the present invention;

FIG. 5 is a plan view of a still further embodiment of the preassembled intra-oral disposable rubber dam device of the present invention;

FIG. 6 is a cross-sectional view of a rib of the rubber dam device shown in FIG. 5;

FIG. 9 is a perspective view of a further embodiment of the preassembled intra-oral disposable rubber dam device of the present invention.

DETAILED DESCRIPTION OF THE PREFERRED EMBODIMENTS

Figure 7:
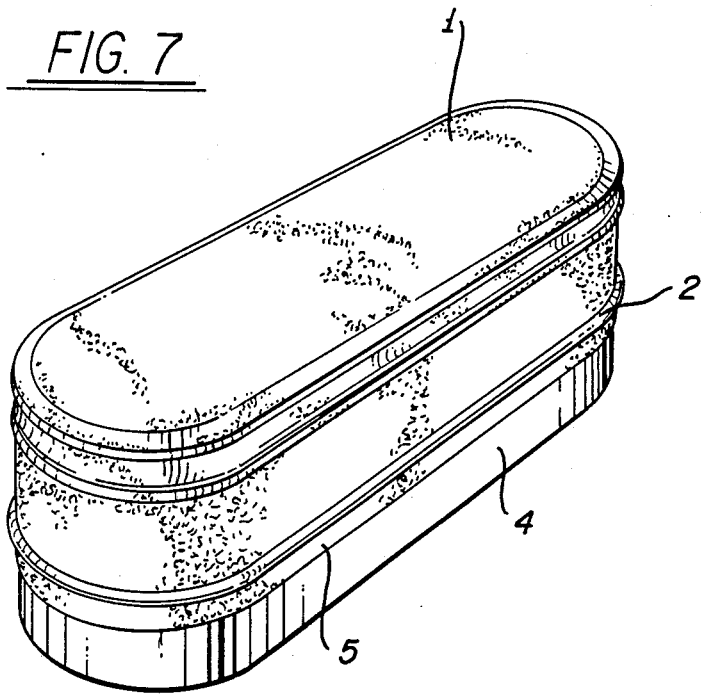
FIG. 7 is a perspective view of a preformed elastic skin and preformed frame member positioned over a form used in a process for assembling the disposable rubber dam device of the present invention.
Figure 8:
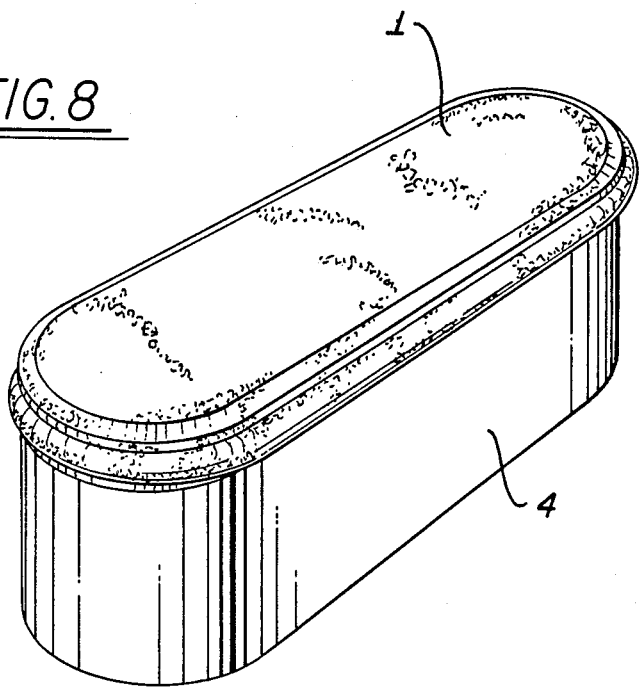
FIG. 8 is a perspective view of a partially assembled disposable rubber dam device of the present invention.

Referring to the drawings, the preassembled intra-oral disposable rubber dam device of the present invention is a unitary structure comprising two basic components, namely, a shaped elastic membrane 1 and a complementary annular spring-like frame member 2. The peripheral portion of the elastic membrane 1 is wrapped around the spring-like frame member 2 and secured in place by adhesive 3 (see FIG. 3) in a manner described below. The spring-like frame member 2 serves to support the portion of the elastic membrane 1 contained within the perimeter of the spring-like frame member in a taut position.

An important characteristic of the rubber dam device of the present invention is that it may be folded as required (see FIG. 1) without permanently distorting the dam due to the nature of the spring-like frame member. The rubber dam device, in the absence of any distorting pressure being applied, will normally be retained by the spring-like frame member in a flat planar configuration as shown, for example, in FIG. 2. When the rubber dam device is folded as shown in FIG. 1 or even folded more severly and in more locations than in FIG. 1, the spring-like frame member biases the rubber dam towards the substantially flat configuration.

The elastic membrane 1, which for example may be composed of latex rubber, should ideally have the following properties within the ranges as specified:

| Thickness | 0.005–0.100 inch |
| Hardness | 70–90A (Shore) |
| Ultimate elongation | 500–1000 percent |
| Ultimate tensile strength | 3000–9000 psi |
| Specific gravity | 1.03–1.15 |
| VICAT softening point | At least 140° F. |
| Melt temperature | At least 280° F. |
| Notched resistance to tearing | At least 120 kilonewtons/meter |

The annular spring-like frame member 2 may be composed of any material, such as a metal or a plastic, which has the necessary resilience as determined by the following characteristics:

| Hardness | 55 to 75 D (Shore) |
| Ultimate elongation | 250 to 500 percent |
| Ultimate tensile strength | 6000–9000 psi |
| Flexural modulus | 50,000–200,000 psi |

A preferred annular spring-like frame member composition is a plastic material in cord form such as a low-density polyethylene or a polyether block amide (PEBA) having the generalized chemical formula

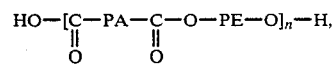

where PA represents the polyamide segment and PE represents the polyether segment. A commercially available low-density polyethylene suitable for the annular spring-like frame has a nominal 0.918 grams per cubic centimeter density and a nominal 1.2 grams per ten minutes melt index. The plastic cord ideally has a thickness range from about 0.050 to 0.250 inch. Ideal characteristics of the plastic cord or ring are as follows:

| Hardness | 55 to 75 D (Shore) |
| Ultimate elongation | 250 to 500 percent |
| Ultimate tensile strength | 6000–9000 psi |
| Specific gravity | 1.01–1.25 |
| Flexural modulus | 50,000–200,000 psi |
| VICAT softening point | At least 140° F. |
| Melt temperature | At least 280° F. |

Both the elastic membrane and the plastic annular spring-like frame member should maintain the above properties over an extended period of time. The above properties of the elastic membrane and plastic frame member should not be substantially affected when subjected to exposure, for the purpose of sterilization, to cobalt 60 at 2½ Megarad. After two weeks there should be no more than a 1 to 2 percent loss of the above properties, after seven weeks the loss in the above properties should be less than 5 to 8 percent, and after fifteen months there should be no further loss of the above properties. Furthermore, the shelf life for the membrane should be at least nine months.

The preformed elastic membrane and annular spring-like frame member may be formed and assembled in any convenient manner without departing from the present invention. The following is a description of a best mode for producing the elastic membrane and the annular plastic cord spring-like frame member and for assembling these to form the preassembled intra-oral disposable rubber dam device of the present invention.

A latex rubber membrane may be made on a computer-generated shaped mold having a substantially flat surface of predetermined peripheral shape and side surfaces extending transversely from the periphery of the flat surface. The computer-generated shape is calculated on the basis of measurements from various human oral cavities displayed in one mathematical plane. The mold is momentarily dipped into a liquefied latex rubber mixture to form a film in the mold flat and side surfaces. The mold with the film is then placed in an oven to dry and cure the latex rubber mixture to form the membrane. The membrane is then stripped from the mold, rinsed with a solution of cornstarch and water and dried.

An annular plastic cord spring-like frame member may be formed, for example, by injecting molten low-density polyethylene under high pressure into a computer-generated shaped mold. The frame member in relaxed position has substantially the same shape as the peripheral shape of the flat surface of the mold for forming the membrane.

Referring to FIG. 7, the preformed latex membrane 1 may be stretched over a mold 4 having a top surface configuration substantially the same as that of the rubber dam device as assembled. (The mold 4 has substantially the same configuration as the mold on which the latex membrane 1 was formed.) The annular plastic cord spring-like frame member 3 is then placed over the membrane 1 and mold 4 and positioned adjacent the end 5 of the skirt portion of the membrane. The end 5 of the skirt portion is then lapped over and tucked under the annular plastic cord spring-like frame member 2 after which the frame member 2, covered with the membrane 1, is rolled upwardly on the mold 4. As it is rolled, the frame member, with the rolled portion of the skirt, is grabbed and pulled downward on the mold to continually keep the membrane stretched and taut. When the frame member reaches a point approximately one-half revolution from the top surface of the mold, it is retained in an annular groove on the surface of the mold and a cement or adhesive, such as a liquid cyanoacrylate ester, is applied with a pinpoint nozzle applicator to the crease between the rolled portion of the latex membrane containing the frame member on the one side and the unrolled portion of the latex membrane on the other around the entirety of the mold. The frame member is then rolled the final one-half revolution to the top of the mold. The assembly is allowed to air-dry for approximately one minute and then stripped from the mold. Thus, the preassembled intra-oral disposable rubber dam device of the present invention is formed.

The preassembled intra-oral disposable rubber dam device of the present invention as produced above may be washed prior to non-sterile packaging or can be sterilized and then individually sterile-packed for distribution to dentists and dental technicians.

In use, the dentist or dental technician, if he/she desires to isolate one tooth or a series of teeth, may use a standard rubber dam punch or other sharp device to cut one or more small holes in the membrane 1 medial to the frame member 2 of the disposable rubber dam device, the location of the one or more holes corresponding to the one or more teeth to be isolated. A smear of lubricant over the one or more holes is recommended for easier installation. The disposable rubber dam device is then folded in half, squeezed into fourths and inserted into the oral cavity of the patient. The device acts in the manner of a spring and reopens itself to the half-folded position shown in FIG. 1, due to the resilient nature of the spring-like frame member 2. This spring or restoring action continues to cause the rubber dam device to tend to open itself to its original flat position shown in FIG. 2. This restoring action forces the patient's mouth open and maintains the mouth in the open position. The frame member fits radially to the teeth. If the patient has a small mouth and the dentist or dental technician has difficulty inserting the device, or if the patient is an acute gagger, the patient can be quickly taught to insert the device himself/herself.

Once the device is positioned in the oral cavity, the dentist or dental technician can complete the installation of the device by stretching the punched membrane around the one or more teeth to be isolated. The frame spring action pushes the membrane with a maximum force around the one or more teeth such that the membrane is held taut beneath the border of the crown-gum line of the one or more teeth being isolated. Dental floss may be used by the dentist or dental technician to force the membrane material around occluded teeth. No clamps are necessary to hold the disposable rubber dam device or the membrane itself around the one or more teeth being isolated. One exception to this feature is that if the dentist or dental technician desires to isolate a partially erupted tooth, a clamp may be used to assist the frame member spring action in keeping the membrane around the tooth and beneath the border of the crown-gum line. In no event is an external or internal frame required.

If the dentist or dental technician desires to install the device in a totally intra-oral fashion, he/she may punch the one or more holes at the respective locations in the elastic membrane to facilitate such installation. If the dentist or dental technician desires to install the device such that a tooth or a series of teeth may be isolated and additionally the upper or lower lips are to be covered and retracted, he/she may punch the one or more holes in the corresponding one or more positions in the elastic membrane such that when the disposable rubber dam device is installed the device protrudes from the oral cavity and covers and retracts the upper lips, lower lips or both; the multi-directional flexibility of the device allowing the device to adjust to any size mouth opening with no comfort loss to the patient.

It will be appreciated that the annular spring-like frame member 2 is designed such that it can be folded at any position along its primary plane axis and still provide the maximum spring force to push the membrane around the one or more teeth and to maintain the membrane away from and beneath the border of the crown-gum line. Also, the annular spring-like frame member 2 serves to press against the inner surfaces of the patient's cheeks to form a seal between the periphery of the rubber dam device and the cheeks, preventing foreign objects and fluids from migrating to other portions of the oral cavity. This feature of the frame member also serves to provide a wider work area for the dentist or dental technician.

Another embodiment of the disposable rubber dam device of the present invention is illustrated in FIG. 4 wherein an annular band portion 6 of thicker membrane is provided medial to the spring-like frame member around the entire periphery of the membrane, the central portion 7 of the membrane being thinner. The preferred width of the band portion 6 may range from 0.125 inch to 1.000 inch, and its thickness may range from 0.010 inch to 0.200 inch. The central portion 7 of the membrane may have a thickness ranging from 0.005 inch to 0.100 inch. A specific example of a membrane of this type has a thickness in the central portion 7 of 0.008 inch and a thickness in the annular band portion 6 of 0.015 inch. The one or more holes punched in the membrane are formed in the thicker band portion 6 of the membrane. This thicker band of membrane prevents possible tearing of the membrane during insertion around occluded or sharp-edged teeth.

A still further embodiment of the invention is shown in FIGS. 5 and 6 wherein the membrane 1 is formed with a series of ribs 8. The ribs are arranged such that a pair of ribs coincide with the location of a tooth. These ribs are arranged along a radial axis perpendicular to and adjacent the spring-like frame member in an annular configuration. Thus, eighteen ribs, a pair for each tooth per upper or lower jaw, are formed in the membrane. A cross-sectional view of a rib 8 is illustrated in FIG. 6. The ribs are triangular in shape, the size of one side of the triangle being about 0.0018 inch. The ribs facilitate installation between occluded teeth and facilitate insertion around wide-parted teeth.

Another embodiment of the disposable rubber dam device of the present invention is illustrated in FIG. 9 wherein the elastic membrane 1 includes an annular extension or wing 9 of the elastic membrane which projects from the frame 2. The wing may be an integral part of the elastic membrane material within and surrounding the frame member or may be a separately formed annular member secured at its inner edge thereof to the frame member or elastic membrane surrounding the frame member by adhesive. This annular wing serves to prevent the liquid excretions from the parotid glands from flowing into the work area in the oral cavity. Also, the annular wing 9 serves to prevent chemicals, such as an acid used in root canal procedures, from splashing against the gums and inner surfaces of the cheeks of the patient.

Although certain preferred embodiments of the invention have been disclosed for purposes of illustration, it will be evident that various changes and modifications may be made therein which fall within the scope of the present invention.

I claim:

1. A unitary preassembled intra-oral disposable rubber dam device comprising an annular, resilient frame member and a flexible, elastic membrane, said annualar frame member having a predetermined configuration, a memory characteristic such that when pressure applied to distort said frame member is relaxed said frame member returns to substantially said predetermined configuration, and the following physical characteristics:

| Hardness | 55 to 75 D (Shore) |
|---|---|
| Ultimate elongation | 250 to 500 percent |
| Ultimate tensile strength | 6000–9000 psi |
| Flexural modulus | 50,000–200,000 psi, | the perimeter of said membrane being secured to said frame member such that said membrane is held taut by said frame member.

2. A unitary preassembled intra-oral disposable rubber dam device according to claim 1 wherein said annular frame member comprises a polymeric material.

3. A unitary preassembled intr-oral disposable rubber dam device according to claim 2 wherein said polymeric material is a low-density polyethylene.

4. A unitary preassembled intra-oral disposable rubber dam device according to claim 2 wherein said polymeric annular frame member has the following physical characteristics:

| Hardness | 55 to 75 D (Shore) |
|---|---|
| Ultimate elongation | 250 to 500 percent |
| Ultimate tensile strength | 6000–9000 psi |
| Specific gravity | 1.01–1.25 |
| Flexural modulus | 50,000–200,000 psi |
| VICAT softening point | At least 140° F. |
| Melt temperature | At least 280° F. |

5. A unitary preassembled intra-oral disposable rubber dam device according to claim 1 wherein the cross-sectional thickness of said frame member ranges between 0.050 and 0.250 inch.

6. A unitary preassembled intra-oral disposable rubber dam device according to claim 1 wherein said membrane is a shaped latex rubber membrane.

7. A unitary preassembled intra-oral disposable rubber dam device according to claim 6 wherein said latex rubber membrane has physical characteristics falling within the following ranges:

| Thickness | 0.005–0.100 inch |
|---|---|
| Hardness | 70–90A (Shore) |
| Ultimate elongation | 500–1000 percent |
| Ultimate tensile strength | 3000–9000 psi |
| Specific gravity | 1.03–1.15 |
| VICAT softening point | At least 140° F. |
| Melt temperature | At least 280° F. |
| Notched resistance to tearing | At least 120 kilonewtons/meter |

8. A unitary preassembled intra-oral disposable rubber dam device comprising an annular, resilient frame member and a flexible, elastic membrane, said annular frame member having a predetermined configuration and a memoury characteristic such that when pressure applied to distort said frame member is relaxed said frame member returns to substantially said predetermined configuration, the perimeter of said flexible, elastic membrane being coiled about said frame member and secured thereto such that said membrane is held taut by said frame member.

9. A unitary preassembled intra-oral disposable rubber dam device comprising an annular, resilient frame member and a flexible, elastic membrane, said annualar frame member having a predetermined configuartion and a memory characteristic such that when pressure applied to distort said frame member is relaxed said frame member returns to substantially said predetermined configuration, the perimeter of said membrane being secured to said frame member such that said membrane is held taut by said frame member, and annular band portion of said flexible, elastic membrane adjacent said frame member having a cross-sectional thickness greater than the thickness of the remaining portion of said membrane within said annular band portion to prevent tearing of said membrane during its insertion around occluded or sharp-edged teeth.

10. An intra-oral disposable rubber dam device according to claim 11 wherein the thickness of said annular band portion is between 0.010 and 0.200 inch, the thickness of said remaning portion of said membrane is between 0.005 and 0.100 inch, and the width of said annular band portion is between 0.125 and 1.000 inch.

11. A unitary preassembled intra-oral disposable rubber dam device comprising an annular, resilient frame member and a flexible, elastic membrane, said annular frame member having a predetermined configuration and a memory characteristic such that when pressure applied to distort said frame member is relaxed said frame member returns to substantially said predetermined configuration, the perimeter of said membrane being secured to said frame member such that said membrane is held taut by said frame member, said membrane being formed with a plurality of generally radially extending ribs therein arranged in an annular pattern adjacent said frame member, each adjacent pair of ribs coinciding with the location of a patient's tooth such that, upon pressing said membrane over a tooth to cause said tooth to project through an aperture in said membrane between said pair of ribs, insertion of said membrane between occluded teeth and around wide-parted teeth is facilitated.

12. A unitary preassembled intra-oral disposable rubber dam device comprising an annular, resilient frame member; a flexible, elastic membrane, said annular frame member having a predetermined configuration and a memory characteristic such that when pressure applied to distort said frame member is relaxed said frame member returns to substantially said predetermined configuration, said membrane being secured to said frame member such that the portion of said membrane within said annular frame member is held taut by said frame member; and a narrow annular membrane projecting about said annular frame member, whereby when said dam device is placed in a patient's oral cavity said annular membrane prevents excretions from the parotid glands from flowing into the work area in the oral cavity and prevents chemicals used in treatment from splashing against the gums and inner surfaces of the cheeks of the patient.

* * * * *